United States Patent [19]

Baum et al.

[11] Patent Number: 5,204,441

[45] Date of Patent: Apr. 20, 1993

[54] POLYFLUORINATED, BRANCHED-CHAIN DIOLS AND DIISOCYANANTES AND FLUORINATED POLYURETHANES PREPARED THEREFROM

[75] Inventors: Kurt Baum, Pasadena; Thomas G. Archibald, Los Angeles; Aslam A. Malik, San Dimas, all of Calif.

[73] Assignee: Fluorochem Inc., Azusa, Calif.

[21] Appl. No.: 491,972

[22] Filed: Mar. 12, 1990

[51] Int. Cl.$^5$ .................. C08G 18/28; C08G 18/32
[52] U.S. Cl. .................................. 528/70; 528/63; 570/181
[58] Field of Search ............ 528/70, 63; 526/247; 525/326.3; 570/181

[56] References Cited

U.S. PATENT DOCUMENTS

| | | | |
|---|---|---|---|
| 4,487,903 | 12/1984 | Tatemoto et al. | 526/247 |
| 4,942,164 | 7/1990 | Baum et al. | 528/70 |
| 5,043,410 | 8/1991 | Re et al. | 528/70 |

*Primary Examiner*—Morton Foelak
*Assistant Examiner*—Duc Truong
*Attorney, Agent, or Firm*—John H. Crowe

[57] ABSTRACT

Branched-chain diols and a method of forming them by reacting 1,4-diiodoperfluorobutane and perfluoropropylene to obtain branched-chain diiodide adducts thereof, reacting the diiodide adducts with ethylene to obtain I—$CH_2CH_2$—R—$CH_2CH_2$—I, wherein R is a branched-chain perfluoroalkyl radical, and hydrolysing the iodo groups to alcohols to obtain HO—$CH_2CH_2$—R—$CH_2CH_2$—OH. These diols can be reacted with branched-chain diisocyanates to form polyurethanes of better processability and lower glass transition temperatures than polyurethanes prepared from linear fluorinated monomers.

5 Claims, No Drawings

POLYFLUORINATED, BRANCHED-CHAIN DIOLS AND DIISOCYANANTES AND FLUORINATED POLYURETHANES PREPARED THEREFROM

The Government has rights in this invention pursuant to contracts N00014-84-C-0388, N00014-87-C-0797 and N00014-88-C-0158, awarded by the Office of Naval Research.

BACKGROUND OF THE INVENTION

This invention relates generally to polyfluorinated, branched-chain diols and diisocyanates, methods of synthesizing them and polyurethanes prepared therefrom.

Fluorine is known to impart useful properties to polymers, including thermal stability, low-temperature flexibility, solvent resistance, marine antifouling properties, etc. Also, polyurethanes are known to be one of the most versatile of the polymer systems. Mixtures of diols and diisocyanates can be cured to polyurethanes at low temperatures, and the degree of cross linking can be controlled by adding varying amounts of triols.

A method of synthesizing perfluoroalkylene bis(ethylamines) having the formula $NH_2-CH_2CH_2-(CF_2)_n-CH_2CH_2-NH_2$, wherein n is a whole number of from 4 to 16, inclusive, is disclosed in U.S. patent application Ser. No. 07/202,505, filed Jun. 6, 1988, by Paul G. Cheng and one of the present applicants (Kurt Baum), which is a division of U.S. patent application Ser. No. 07/020,361, filed Mar. 2, 1987. Both of those applications contain subject matter presently under a Secrecy Order, although the parent application is now abandoned and the divisional application is slated to be abandoned for failure of applicants to respond to an Office action thereon. More specifically, the method of synthesizing diamines disclosed in these two patent applications takes the following route.

$$I(CF_2)_nI + CH_2=CH_2 \longrightarrow$$
$$I-CH_2CH_2-(CF_2)_n-CH_2CH_2-I$$
$$\xrightarrow{NaN_3}$$
$$N_3-CH_2CH_2-(CF_2)_n-CH_2CH_2-N_3 \xrightarrow{H_2}$$
$$NH_2-CH_2CH_2-(CF_2)_n-CH_2CH_2-NH_2$$

Copending U.S. patent application Ser. No. 07/350,130, filed May 8, 1989, by Baum, Malik, and Tzeng (Baum and Malik being two of the present applicants), discloses a method of converting the aforesaid diamines to diisocyanates by first bubbling gaseous hydrogen chloride into suspensions of the diamines in a suitable solvent, then introducing phosgene at temperatures up to 130° C. to form the diisocyanates. That copending application also discloses that analogous monofunctional isocyanates can be prepared by the same reaction scheme. Such monofunctional isocyanates are potentially useful for fabric soil-resistance treatment by reacting with hydroxyl groups in the fabric.

Diols having the formula $HO-CH_2CH_2-(CF_2)_n-CH_2CH_2-OH$, in which n is 4 or 6, have been reported, and similar diols where n is from 1 to 20 have been claimed in a Japanese patent (Asahi Glass Co., *Jpn. Kokai Tokkyo Koho* JP 82 99,552, Jun. 21, 1982).

The reaction of perfluoropropylene with 1,4-diiodoperfluorobutane has been reported to give a mixture of telomers (G. Caporiccio, G. Bargigia, C. Tonelli and V. Tortelli, *Eur. Pat. Appl.* EP 200,908, December 1986; *Chem Abstr.*, 107 6762.

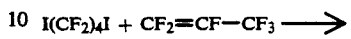

$$I(CF_2)_4I + CF_2=CF-CF_3 \longrightarrow$$

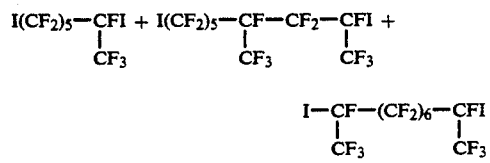

SUMMARY OF THE INVENTION

It would be desirable to obtain diols with similar or higher fluorine content than those claimed in the above-identified Japanese patent, but with higher solubility in other polymer components and, therefore, better processability. We felt that pendant trifluoromethyl groups on the fluorocarbon chain might reduce the tendency toward crystallinity by providing molecular asymmetry. In line with that, we converted perfluoropropylene adducts of the above-illustrated type to diols by reacting them with ethylene, then hydrolyzing their diodo groups to alcohols. Although the addition of primary perfluoroalkyl iodides to ethylene is well known, the ability of branched structures of the present type to undergo the reaction could not be predicted. The simplest example of this series is shown below, starting with the 1:1 adduct of perfluoropropylene and 1,4-diiodoperfluorobutane. This reaction sequence was extended to the 2:1 adduct of perfluoropropylene and 1,4-diiodoperfluorobutane to yield a mixture of isomers. Oligomers containing adducts with more than 2 perfluoropropylene units per 1,4-diiodoperfluorobutane can also be used. The ethylene adducts of all of these diiodofluorocarbons, as well as the resulting alcohols, are new compounds. The starting materials are not limited to adducts of perfluoropropylene with 1,4-diiodoperfluorobutane and the use of higher $\alpha,\omega$-diiodoperfluoroalkanes in place of 1,4-diiodoperfluorobutane is within the scope of this invention. The resulting diols are useful for the preparation of polyurethanes and polyesters.

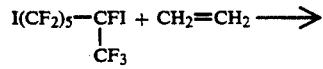

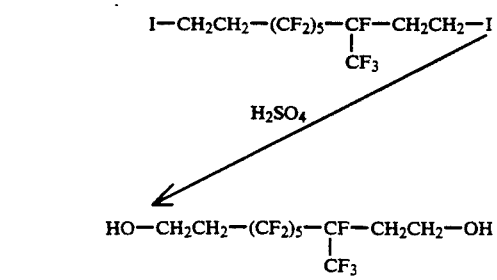

We have, as an aspect of the present invention, also converted the branched ethyleneinserted diiodides to their corresponding diamines by the method of copending patent application Ser. No. 07/202,505, referred to above. The branched diamine products of this reaction are useful for the preparation of branched-chain diisocyanates, as well as polyamides, polyimides, epoxy polymers, etc. The corresponding diisocyanates should yield polyurethanes with improved processability and lower glass transition temperatures, compared to polyurethanes prepared from linear fluorinated diisocyanates. Commercially, oligomeric mixtures of the branched diamines, as well as the diols, would be more costeffective, we felt, than the discrete components, in the production of polymer systems, because this should result in lower glass transition temperatures and more facile processing characteristics. The following reaction scheme illustrates the conversion of the aforesaid diiodides to their corresponding diamines.

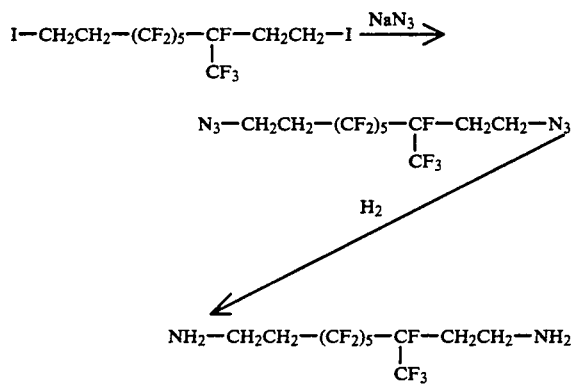

We have prepared polyurethanes by reacting branched-chain diols in accordance with this invention with branched-chain diisocyanates such as disclosed herein. We have also prepared polyurethanes from the following combinations of reactants: branched-chain diols and commercial nonfluorinated diisocyanates; branched-chain diols and linear fluorinated diisocyanates; and linear fluorinated diols with branched-chain fluorinated diisocyanates. Dibutyltin dilaurate was used as a catalyst in some of these reactions, but others were carried out thermally without a catalyst. As for the catalyzed reactions, we do not wish to be limited to dibutyltin dilaurate as a catalyst, because any standard catalyst known to those skilled in the art for such reactions can be used within the scope of our invention. Polyols can be added to the monomer mixtures in such reactions to give cross-linked polymer products.

We have noted that polyurethanes prepared from reactions of branched fluorinated diols with hexamethylene diisocyanate, $OCN-CH_2CH_2-(CF_2)_4-CH_2CH_2-NCO$ or branched-chain diisocyanates are elastomers. These elastomers are excellent adhesives, which adhere readily to metals, glass, and even to PTFE. Polyurethanes resulting from the reactions of branched fluorinated diols with toluene diisocyanate are rigid polymers, as are those from the linear fluorinated diols and any of the above-mentioned diisocyanates.

It is thus a principle object of the present invention to provide novel branched-chain polyfluorinated diols from which polyurethanes with improved processability and lower glass transition temperatures, by comparison with polyurethanes prepared from linear fluorinated reactants, can be prepared.

Another object of the invention is to provide novel branched-chain diisocyanates, also capable of yielding polyurethanes with such improved processability and lower glass transition temperatures.

Still another object of the invention is to provide novel methods of synthesizing such branched chain diols and diisocyanates.

Yet another object of the invention is to provide means for synthesizing polyurethanes with the above-noted characteristics of lower glass transition temperatures and more facile processing characteristics than presently known means of polyurethane production provide.

Other objects, features and advantages of the invention will be apparent to those skilled in the art in the light of present teachings.

DESCRIPTION OF THE PREFERRED EMBODIMENTS

Following are examples included to flesh out the present disclosure. It is to be understood, however, that these examples are offered merely as a means of illustration and are not intended to limit the scope of the invention to the particular combinations of materials, conditions, proportions, etc. set forth therein.

EXAMPLE I

Oligomerization of 1,4-Diiodoperfluorobutane with Perfluoropropylene

A 150-mL stainless steel pressure cylinder containing 1,4-diiodoperfluorobutane (20 g, 44 mmol) was cooled in a dry ice/acetone bath and charged with perfluoropropylene (35 g, 233 mmol). The cylinder was heated at 200° C. for 77 hours, cooled and vented. The residue was dissolved in dichloromethane and washed with saturated aqueous sodium sulfite and brine, dried ($MgSO_4$), and stripped of solvent under reduced pressure to give 31 g of a pink oil. Glc analysis indicated 6 components. Spinning band distillation gave (1) 0.75 g of liquid, bp 25°–30° C. (0.3 mm), (2) 6.4 g, bp 38°–40° C. (0.3 mm), (3) 10 g, bp 58°–60° C. (0.3 mm), (4) 5.0 g, bp 105°–108° C. (0.3 mm) and (5) a residue of 8.5 g. The first fraction consisted mainly of unreacted 1,4-diiodoperfluorobutane. The second fraction was found by glc to be ca. 90% pure 1,6-diiodoperfluoroheptane, $I(CF_2)_5-CF(CF_3)I$; redistillation gave analytically pure material: $^{19}F$ NMR (neat) $\phi$ 62.4 (2 F), 76.0 (3 F), 109.6 (2 F), 115.2 (2 F), 121.2 (2 F), 122.8 (2 F) and 145.6 (1 F); Anal. Calcd for $C_7F_{14}I_2$: C, 13.92; F, 44.05; Found: C, 13.64; F, 44.01. The third distillation fraction was identified as a mixture of 2,9-diiodoperfluorodecane $[ICF(CF_3)(CF_2)_6CF(CF_3)I]$ and 1,8-diiodo-6-trifluoromethylperfluorononane $[ICF(CF_3)-CF_2CF(CF_3)CF_2(CF_2)_4I]$. A sample of $ICF(CF_3)(CF_2)_6CF(CF_3)I$ was isolated by preparative glc: $^{19}F$ NMR ($CDCl_3$) $\phi$ 76.0 (6 F), 110.0 (4 F), 121.2 (4 F), 123.6 (4 F) and 146.0 (2 F). Anal. Calcd for $C_{10}F_{20}I_2$: C, 15.93; F, 50.40. Found: C, 15.83; F, 50.47. The fourth distillation fraction consisted of an isomeric mixture of perfluoroalkyl diiodides with the general formula $I[CF(CF_3)CF_2]_x(CF_2)_4[CF_2CH(CF_3)]_yI$, where $x+y=3$. The distillation residue was found to be a mixture of higher oligomers.

EXAMPLE II

Preparation of
1,10-Diiodo-3-trifluoromethyl-3,4,4,5,5,6,6,7,7,8,8-undecafluorodecane A 150-mL stainless steel pressure cylinder was charged with the 1,6-diiodoperfluoroheptane I(CF$_2$)$_5$—CF(CF$_3$)I (9.4 g, 15.6 mmol) and pressurized to 300 psi with ethylene, and the mixture was heated at 160° C. for 48 hours. Excess ethylene was then released and the residue was dissolved in Freon 113. The organic layer was washed with saturated aqueous sodium sulfite and brine, and dried (MgSO$_4$), and the solvent was evaporated under reduced pressure to give 9.6 g (93%) of 1,10-diiodo-3-trifluoromethyl-3,4,4,5,5,6,6,7,7,8,8-undecafluorodecane, a colorless viscous oil: glc (OV-17, 110° to 220° C. at 16° C./min) R$_T$4.4 min; $^1$H NMR (CDCl$_3$) δ 2.75 (m, 4H) and 3.28 (m, 4H); $^{19}$F NMR (CDCl$_3$) φ 74.5 (3 F), 115.2 (2 F), 117.5 (2 F), 121.0–121.6 (4 F), 123.6 (2 F) and 182.8 (1 F); Anal. Calcd for C$_{11}$H$_8$F$_{14}$I$_2$: C, 20.02; H, 1.22; F, 40.30. Found: C, 20.05; H, 1.25; F, 40.41.

EXAMPLE III

Synthesis of
1,12-Diiodo-3,5-bis(trifluoromethyl)-3,4,4,5,6,6,7,7,8,8,9,9,10,10-tetradecafluorododecane
and
1,12-Diiodo-3,10-bis(trifluoromethyl)-3,4,4,5,5,6,6,7,7,8,8,9,9,10-tetradecafluorododecane A 150-mL stainless steel pressure cylinder was charged with a mixture of 2,9-diiodoperfluorodecane and 1,8-diiodo-6-trifluoromethylperfluorononane (5.6 g, 7.4 mmol) and ethylene (300 psi). The mixture was heated at 160° C. for 48 hours. Excess ethylene was released and the residue was dissolved in dichloromethane. The organic layer was washed with aqueous sodium sulfite and brine, dried, filtered, and solvent was evaporated under reduced pressure to give 5.3 g (89%) of 1,12-diiodo-3,5-bis(trifluoromethyl)-3,4,4,5,6,6,7,7,8,8,9,9,10,10-tetradecafluorododecane and 1,12-diiodo-3,10-bis(trifluoromethyl)-3,4,4,5,5,6,6,7,7,8,8,9,9,10-tetradecafluorododecane, a colorless viscous oil: Glc (SE-30, 160° C.) R$_T$2.6 and 2.9 min; $^1$H NMR (CDCl$_3$) δ 3.28 (m, 4H) and 2.81 (m, 4H); $^{19}$F NMR (CDCl$_3$) φ 70.2, 74.5, 115.2, 117.5, 120.0, 120.8, 121.6, 123.6, and 182.7; Anal. Calcd for C$_{14}$H$_8$F$_{20}$I$_2$: C, 20.75; H, 1.00; F, 46.90. Found: C, 20.76; H, 1.01; F, 46.98.

EXAMPLE IV

Synthesis of an Oligomeric Mixture of
α,ω-Bis(2-iodoethyl)-perfluoroalkanes

A 300 mL stainless steel pressure cylinder was charged with an oligomeric mixture of branched α,ω-diiodoperfluoroalkanes (22 g) and ethylene (350 psi), and heated at 160° C. for 48 h. Excess ethylene was released and the residue was dissolved in Freon 113. The solution was washed with aqueous sodium sulfite and brine, dried, and solvent was evaporated under reduced pressure to give 23.5 g of a colorless viscous oil. Bulb-to-bulb distillation of this oil at 120° C./0.1 mm give 22 g of a mixture of α,ωbis(2-iodoethyl)perfluoroalkanes. Glc analysis revealed that the mixture consisted of 1,10-diiodo-3-trifluoromethyl-3,4,4,5,5,6,6,7,7,8,8-undecafluorodecane (15%), the isomers 1,12-diiodo-3,5-bis(trifluoromethyl)-3,4,4,5,6,6,7,7,8,8,9,9,10,10-tetradecafluorododecane and 1,12-diiodo-3,10-bis(trifluoromethyl)-3,4,4,5,5,6,6,7,7,8,8,9,9,10-tetradecafluorododecane (42%), an isomeric mixture of compounds with the structure I[CF(CF$_3$)CF$_2$]$_x$(CF$_2$)$_4$[CF$_2$CF(CF$_3$)]$_y$I where x+y=3 (35%), and higher oligomer (8%): $^1$H NMR (CDCl$_3$) δ 2.0–2.79 (m); $^{19}$F NMR (CDCl$_3$) φ 72.0, 76.0, 108.0, 112.4, 116.0, 118.0, 121.6, 124.0 and 182.0.

EXAMPLE V

Synthesis of
3-Trifluoromethyl-3,4,4,5,5,6,6,7,7,8,8-undecafluorodecane-1,10-diol A round-bottom flask fitted with a mechanical stirrer, a condenser, and a thermometer was charged with 30% fuming sulfuric acid (175 mL). 1,10-Diiodo-3-trifluoromethyl-3,4,4,5,5,6,6,7,7,8,8-undecafluorodecane (20.0 g, 30.3 mmol) was added over a 15 min period and the mixture was heated at 65° C. for 23 hours. The reaction mixture was quenched over crushed ice and water. Sodium sulfite was added until the iodine color was discharged and the mixture was heated at 85° C. for 22 hours. The product was extracted with diethyl ether and the organic phase was washed with water, aqueous sodium sulfite, sodium carbonate and brine. The organic layer was dried (MgSO$_4$) and concentrated under reduced pressure to give an oil. Bulb-to-bulb distillation (100° C./0.2 mm) of this oil gave 11.1 g (83%) of 3-trifluoromethyl-3,4,4,5,5,6,6,7,7,8,8-undecafluorodecane1,10-diol, a colorless oil: glc (OV-17, 110° to 220° C. at 16° C./min) R$_T$1.9 min; $^1$H NMR (acetone-d$_6$) δ 3.90 (t, J=7 Hz, 4H) and 2.1–2.9 (m, 4H); $^{19}$F NMR (CDCl$_3$) φ 74.4 (3 F), 112.9 (2 F), 117.4 (2 F), 120.1–121.0 (4 F), 123.3 (2 F) and 182.1 (1 F); IR (neat) 3400, 3050, 2975, 1040–1340, and 980 cm$^{-1}$; Anal. Calcd for C$_{11}$H$_{10}$F$_{14}$O$_2$: C, 30.01; H, 2.29; F, 60.43. Found: C, 30.04; H, 2.36; F, 60.42.

EXAMPLE VI

Synthesis of
3,5-Bis(trifluoromethyl)-3,4,4,5,6,6,7,7,8,8,9,9,10,10-tetradecafluorododecane-1,12-diol and
3,10-Bis(trifluoromethyl)-3,4,4,5,5,6,6,7,7,8,8,9,9,10,10-tetradecafluorododecane-1,12-diol A round-bottom flask fitted with a mechanical stirrer, a condenser, and a thermometer was charged with 30% fuming sulfuric acid (55 mL). A mixture of 1,12-diiodo-3,5-bis(trifluoromethyl)-3,4,4,5,6,6,7,7,8,8,9,9,10,10-tetradecafluorododecane and 1,12-diiodo-3,10-bis(trifluoromethyl)-3,4,4,5,5,6,6,7,7,8,8,9,9,10-tetradecafluorododecane (4.6 g, 5.7 mmol) was added over 10 min and the resulting mixture was heated at 65° C. for 24 hours. The reaction was quenched with crushed ice and water. Sodium sulfite was added until the iodine color was discharged and the mixture was heated at 85° C. for 24 hours. The product was extracted with diethyl ether and the ether solution was washed with water, aqueous sodium sulfite, sodium carbonate and brine. The solution was then dried and the solvent was evaporated under reduced pressure to give 2.6 g (76%) of a mixture of title diols, a viscous opaque oil: glc (OV-17, 110° to 220° C. at 16° C./min) 4.8 min; $^1$H NMR (acetone-d$_6$) δ 3.83 (t, J=7 Hz, 4H) and 2.50 (m, 4H); $^{19}$F NMR (CDCl$_3$) φ 68.5, 74.2, 109.8, 111.1, 112.8, 117.2, 119.1, 119.8, 120.9, 123.1, and 182.0; IR (neat)3400, 3050, 2975, 1040–1400, and 1000 cm$^{-1}$. Anal. Calcd for $C_{14}H_{10}$—$F_{20}O_2$: C, 28.49; H, 1.71; F, 64.38. Found: C, 28.65; H, 1.69; F, 64.64.

EXAMPLE VII

Synthesis of an Oligomeric Mixture of Branched α,ω-Bis(2-hydroxyethyl)-perfluoroalkanes A round-bottom flask fitted with a mechanical stirrer, a condenser and a thermometer was charged with 30% fuming sulfuric acid (60 mL). A mixture of α,ω-bis(2-iodoethyl)perfluoroalkanes (5 g) prepared in Example IV was added over 10 min and the mixture was heated at 65° C. for 24 hours. The reaction mixture was quenched with ice. Sodium sulfite was added until the iodine color was discharged and the mixture was heated at 90° C. for 24 hours. The product was extracted with diethyl ether and the ether solution was washed with water, aqueous sodium sulfite, sodium carbonate and brine. The solution was dried ($MgSO_4$) and the solvent was evaporated under reduced pressure to give 3.8 g of a yellowish brown oil. Bulb-to-bulb distillation (140° C./0.1 mm) gave 2.1 g of crude diols. Addition of chloroform precipitated an oil that was redistilled under reduced pressure to give 1.75 g of a mixture of branched α,ω-bis(2-hydroxyethyl)perfluoroalkanes. Glc analysis (OV-17, 110° to 220° C. at 16° C./min) revealed it was a mixture of 3-trifluoromethyl-3,4,4,5,5,6,6,7,7,8,8-undecafluorodecane-1,10-diol (15%), 3,5-bis(trifluoromethyl)-3,4,4,5,6,6,7,7,8,8,9,9,10,10-tetradecafluorododecane-1,12-diol and 3,10-bis(trifluoromethyl)-3,4,4,5,5,6,6,7,7,8,8,9,9,10-tetradecafluorododecane-1,12-diol (45%), $HOCH_2CH_2$—$[CF(CF_3)CF_2]_x$—$(CF_2)_4$—$[CF_2CF(CF_3)]_y$—$CH_2CH_2OH$ (35%), and higher oligomeric diols (5%): IR (neat) 3400, 3025, 2975, 1360–1040 and 1000 $cm^{-1}$; $^1H$ NMR (acetone-$d_6$) δ 3.80 (br t, 4H) and 2.03–2.75 (br m, 4H); Mol. Wt. ($^1H$ NMR) 750; Anal. Found: C, 28.4; H, 1.61; F, 64.35.

EXAMPLE VIII

Preparation of 1,10-Diazido-3-trifluoromethyl-3,4,4,5,5,6,6,7,7,8,8-undecafluorodecane Sodium azide (300 mg, 4.6 mmol) was added in small portions over a 4 hour period to a solution of 1,10-diiodo-3-trifluoromethyl-3,4,4,5,5,6,6,7,7,8,8-undecafluorodecane (1.1 g, 1.7 mmol) in freshly distilled DMSO (18 mL). The mixture was stirred at room temperature for 24 hours. More sodium azide (150 mg) was added and the mixture was stirred at room temperature for an additional 24 hours. The reaction mixture was diluted with diethyl ether and slowly poured over crushed ice and water containing a few drops of concentrated hydrochloric acid (Caution: $HN_3$ is evolved). The organic layer was separated and the aqueous layer was extracted with diethyl ether. The combined organic solutions were washed with water, 10% HCl, aqueous sodium sulfite and brine and dried ($MgSO_4$). The solvent was evaporated under reduced pressure to give a yellow oil. Distillation gave a forerun, bp 50°–75° C. (0.1 mm) consisting mainly of 1-azido-3-trifluoromethyl-3,4,4,5,5,6,6,7,7,8,8-undecafluoro-9-decene [Glc (OV-17, 110° C. to 200° C. at 16° C./min) $R_T$ 1.24; $^1H$ NMR ($CDCl_3$) δ 5.53 (m), 3.40 (t, J=6 Hz) and 2.30 (m)], and 0.458 g (55%) of 1,10-diazido-3-trifluoromethyl-3,4,4,5,5,6,6,7,7,8,8-undecafluorodecane: bp 85°–100° C. (0.1 mm); glc (OV-17, 100° C. to 220° C. at 16° C. per min) $R_T$3.75; IR ($CDCl_3$) 3050, 2975, 2150 (s), and 1100–1380 $cm^{-1}$; $^1H$ NMR ($CDCl_3$) δ 3.46 (t, J=6 Hz, 4H) and 2.30 (m, 4H). Anal. Calcd for $C_{11}H_8F_{14}N_6$: C 26.95; H, 1.64. Found: C, 27.07; H, 1.67.

EXAMPLE IX

Synthesis of 1,12-Diazido-3,5-bis(trifluoromethyl)-3,4,4,5,6,6,7,7,8,8,9,9,10,10-tetradecafluorododecane and 1,12-Diazido-3,10-bis(trifluoromethyl)-3,4,4,5,5,6,6,7,7,8,8,9,9,10-tetradecafluorododecane Sodium azide (1.2 g, 18.5 mmol) was added to a suspension of 1,12-diiodo-3,5-bis(trifluoromethyl)-3,4,4,5,6,6,7,7,8,8,9,9,10,10-tetradecafluorododecane and 1,12-diiodo-3,10-bis(trifluoromethyl)-3,4,4,5,5,6,6,7,7,8,8,9,9,10-tetradecafluorododecane (7.05 g, 8.64 mmol) in DMSO (67 mL, freshly distilled) and dichloromethane (23 mL). The mixture was stirred at room temperature for 24 hours. A second portion of sodium azide (1.3 g, 20 mmol) was added and the mixture was stirred at room temperature for an additional 24 hours. The reaction mixture was diluted with diethyl ether and slowly poured over crushed ice, water, and a few drops of concentrated hydrochloric acid. The organic layer was separated and the aqueous layer was extracted with diethyl ether. The ethereal extracts were combined and washed with water, 10% HCl, aqueous sodium sulfite, and brine. The solution was dried and the solvent was evaporated under reduced pressure to give 5.2 g of a yellow oil. Bulb-to-bulb distillation gave a forerun at 70°–80° C. (0.1 mm), consisting mainly of the azidoalkene [$^1H$ NMR ($CDCl_3$) δ 5.6–5.73 (m, 3H), 3.43 (t, J=6 Hz, 2H) and 2.40 (m, 2H)], followed by the title diazides at 90°–120° C. (0.1 mm): IR ($CDCl_3$) 3050, 2975, 2150 (s), and 1100–1400 $cm^{-1}$; $^1H$ NMR ($CDCl_3$) δ 3.46 (t, J=6 Hz, 4H) and 2.36 (m, 4H).

EXAMPLE X

Preparation of 1,10-Diamino-3-trifluoromethyl-3,4,4,5,5,6,6,7,7,8,8-undecafluorodecane A mixture of 1,10-diazido-3-trifluoromethyl-3,4,4,5,5,6,6,7,7,8,8-undecafluorodecane (7.2 g, 14.7 mmol), methanol (40 mL), Pearlman's catalyst (0.6 g) and a solution of hydrazine (1.1 g, 36 mmol) in methanol (5 mL) was heated under reflux for 21 hours. The mixture was diluted with methanol and filtered through a pad of celite. Methanol was evaporated and the residue was distilled to give 2.5 g (39%) of 1,10-diamino-3-trifluoromethyl-3,4,4,5,5,6,6,7,7,8,8-undecafluorodecane, a colorless oil; bp 0.2 mm, 85°–95° C./0.2 mm; Glc (OV-17, 110° C. to 260° C. at 16° C./min) $R_T$5.4 min; IR (neat) 3350, 3050, 2975 and 1050–1380 $cm^{-1}$; $^1H$ NMR ($CDCl_3$) δ 3.0 (t, J=6 Hz, 4H), 2.20 (m, 4H) and 1.23 (s, 4H). Anal Calcd for $C_{11}H_{12}F_{14}N_2$: C, 30.15; H, 2.76; F, 60–70. Found: C, 29.85; H, 2.36; F, 60.32.

EXAMPLE XI

Synthesis of 1,12-Diamino-3,5-bis(trifluoromethyl)-3,4,4,5,6,6,7,7,8,8,9,9,10,10-tetradecafluorododecane and 1,12-Diamino-3,10-bis(trifluoromethyl)-3,4,4,5,5,6,6,7,7,8,8,9,9,10-tetradecafluorododecane Pearlman's catalyst (0.5 g) was added to a solution of 1,12-diazido-3,5-bis(trifluoromethyl)-3,4,4,5,6,6,7,7,8,8,9,9,10.10-tetradecafluorododecane and 1,12-diazido-3,10-bis(trifluoromethyl)-3,4,4,5,5,6,6,7,7,8,8,9,9,10-tetradecafluorododecane (2.9 g, 4.5 mmol) in methanol (30 mL) and the mixture was hydrogenated in a Parr apparatus, under 30 psi of hydrogen, at room temperature for 24 hours. The mixture was diluted with methanol, filtered through Celite, and solvent was evaporated under reduced pressure to give 2.4 g (92%) of crude diamine. Bulb-to-bulb distillation (0.3 mm/105°–120° C.) gave 0.90 g (35%) of a mixture of 1,12-diamino-3,5-bis(trifluoromethyl)-3,4,4,5,6,6,7,7,8,8,9,9,10,10-tetradecafluorododecane and 1,12-diamino-3,10-bis(trifluoromethyl)-3,4,4,5,5,6,6,7,7,8,8,9,9,10,10-tetradecafluorododecane, a colorless, viscous oil: IR (neat) 3350, 3050, 2975, and 1000–1380 cm$^{-1}$; $^1$H NMR (CDCl$_3$) δ 2.92 (t, J=6 Hz, 4H), 2.20 (m, 4H) and 1.26 (s, 4H). Anal. Calcd for C$_{14}$H$_8$F$_{20}$N$_2$: C, 28.59; H, 2.05; F, 64.60. Found: C, 28.90; H, 2.07; F, 64.32.

EXAMPLE XII

Preparation of Polyurethane from 3,3,4,4,5,5,6,6-Octafluorooctane-1,8-diisocyanate and 1,10-Dihydroxy-3-trifluoromethyl-3,4,4,5,5,6,6,7,7,8,8-undecafluorodecane A mixture of 3,3,4,4,5,5,6,6-octafluorooctane-1,8-diisocyanate (349.3 mg, 1.0267 mmol) and 1,10-dihydroxy-3-trifluoromethyl-3,4,4,5,5,6,6,7,7,8,8-undecafluorodecane (450.6 mg, 1.0236 mmol) was heated at 40° C. for 30 min to form a homogeneous mixture. Dibutyltin dilaurate (10 μL of 0.083M solution in dichloromethane) was added and the mixture was heated at 50° C. for 2 hours. The temperature was increased to 60° C. over 2 hours and then maintained at 60° C. for an additional 8 hours. The polymer, a transparent elastomer, was soluble in boiling acetone, boiling ethyl acetate, and hot (ca. 60° C.) DMF. The polymer became soft at ca. 70° C., melted at 120°–135° C., and underwent decomposition at ca. 280° C.: IR (thin film) 3450, 3025, 1710, 1550, and 1360–1050 cm$^{-1}$; inherent viscosity 0.222 (DMF, 30° C., 0.251 g/100 ml).

EXAMPLE XIII

Preparation of Polyurethane from Toluene Diisocyanate and 1,10-Dihydroxy-3-trifluoromethyl-3,4,4,5,5,6,6,7,7,8,8-undecafluorodecane A mixture of toluene diisocyanate (185 mg, 1.062 mmol) and 1,10-dihydroxy-3-trifluoromethyl-3,4,4,5,5,6,6,7,7,8,8-undecafluorodecane (446 mg, 1.060 mmol) was heated at 70° C. for 15 min to form a homogeneous mixture. Dibutyltin dilaurate (8 μL of 0.20M solution in dichloromethane) was added and the mixture was heated at 68° C. for 17 hours. The resulting transparent yellow solid polymer was sparingly soluble in boiling acetone and boiling ethyl acetate and readily soluble in hot (75° C.) DMF. The material became flexible at 60°–70° C., softened at 105°–115° C., melted at 200°–210° C., and decomposed at ca. 270° C.: IR (thin film) 3400, 3075, 3025, 1725, and 1660–1050 cm$^{-1}$.

EXAMPLE XIV

Preparation of Polyurethane from Toluene Diisocyanate and a Mixture of 3,5-Bis(trifluoromethyl)-3,4,4,5,6,6,7,7,8,8,9,9,10,10-tetradecafluorododecane-1,12-diol and 3,10-Bis(trifluoromethyl)-3,4,4,5,5,6,6,7,7,8,8,9,9,10-tetradecafluorododecane-1,12-diol A mixture of toluene diisocyanate (171 mg, 0.982 mmol) and the title diols (557 mg, 0.978 mmol) was heated to form a homogeneous mixture. Dibutyltin dilaurate (6 μL of 0.20M solution in dichloromethane) was added and the mixture was allowed to react at ambient temperature for 24 hours and then at 56° C. for 14 hours. The product, a transparent yellow-colored rigid polymer, was soluble in boiling acetone and hot (85° C.) DMF. The material became flexible at 60°–65° C., softened at 110°–115° C., melted at 210°–215° C., and decomposed at ca. 260°C.: IR (thin film) 3400, 3050, 3000, 1720, 1660, 1550, and 1000–1400 cm$^{-1}$; inherent viscosity 0.121 (DMF, 30° C., 0.253 g/100 ml).

EXAMPLE XV

Preparation of Polyurethane from 3,3,4,4,5,5,6,6-Octafluorooctane-1,8-diisocyanate and a Mixture of 3,5-Bis(trifluoromethyl)-3,4,4,5,6,6,7,7,8,8,9,9,10,10-tetradecafluorododecane-1,12-diol and 3,10-Bis(trifluoromethyl)-3,4,4,5,5,6,6,7,7,8,8,9,9,10-tetradecafluorododecane-1,12-diol.

A mixture of 3,3,5,5,6,6,7,7-octafluorooctane-1,8-diisocyanate (479 mg, 1.408 mmol) and title diols (828 mg, 1.403 mmol) was heated at 50° C. to form a homogeneous mixture. Dibutyltin dilaurate (10 μL of 0.20M solution in dichloromethane) was added and the mixture was allowed to react at ambient temperature for 24 hours and at 56° C. for 14 hours. The polymer, a transparent rubber, was soluble in boiling acetone, boiling ethyl acetate, and hot (ca 75° C.) DMF; it was insoluble in methanol, Freon 113, and toluene. The polymer softened at 95°–100° C., melted at 200° C. and decomposed at ca. 275° C.: IR (thin film) 3400, 3025, 1700, 1520, and 1000–1400 cm$^{-1}$; inherent viscosity 2.39 (DMF, 30° C., 0.0076 g/100 ml).

EXAMPLE XVI

Preparation of Polyurethane from Hexamethylene Diisocyanate and a Mixture of 3,5-Bis(trifluoromethyl)-3,4,4,5,6,6,7,7,8,8,9,9,10,10-tetradecafluorododecane-1,12-diol and 3,10-Bis(trifluoromethyl)-3,4,4,5,5,6,6,7,7,8,8,9,9,10-tetradecafluorododecane-1,12-diol.

A mixture of hexamethylene diisocyanate (169 mg, 1.006 mmol) and the title diols (594 mg, 1.006 mmol) was heated at 45° C. to form a homogeneous mixture. Dibutyltin dilaurate (5 μL of 0.2M solution in dichloromethane) was added and the mixture was allowed to react at ambient temperature for 24 hours and at 56° C. for 14 hours. The polymer, a transparent rubber, was soluble in boiling acetone, boiling ethyl acetate, and hot (70° C.) DMF. The polymer softened at 115°–120° C., melted at 200°–210° C., and decomposed at ca. 270° C.: IR (thin film) 3400, 3000, 2975, 1660, and 1100–1400 cm$^{-1}$; inherent viscosity 0.344 (DMF, 30° C., 0.262 g/100 ml).

EXAMPLE XVII

Synthesis of 3-Trifluoromethyl-3,4,4,5,5,6,6,7,7,8,8-undecafluorodecane-1,10-diisocyanate.

Hydrogen chloride gas was bubbled through a suspension of 1,10-diamino-3-trifluoromethyl-3,4,4,5,5,6,6,7,7,8,8-undecafluorodecane dihydrochloride (3.3 g, 6.4 mmol) in 1,2-dichlorobenzene (50 mL) for 5 min. Next, phosgene was bubbled through the mixture and the temperature was increased gradually to 130° C. When a homogeneous solution was obtained, excess phosgene was flushed from the reaction mixture with argon and 1,2-dichlorobenzene removed by distillation (30°–32° C./0.2 mm-Hg). The residue was distilled (130°–140° C./0.2 mm) to give 1.7 g (55%) of 3-trifluoromethyl-3,4,4,5,5,6,6,7,7,8,8,-undecafluorodecane-1,10-diisocyanate: glc (OV-101, 100° C. to 280° C. at 16° C./min) $R_T$ 8.14 min; H NMR (CDCl$_3$) $\delta$ 3.549 (m, 4H) and 2.33 (m, 4H); $^{19}$F NMR (CDCl$_3$) $\delta$ −75.2 (3 F), −114.65 (2 F), −117.96 (2 F), −120.9 (2 F), −121.65 (2 F), −123.88 (2 F), and −85.25 (1 F). Anal. Calcd for $C_{13}H_8F_{14}N_2O_2$: C, 31.85; H, 1.64; N, 5.71. Found: C, 31.74; H, 1.45; N, 5.66.

EXAMPLE XVIII

Preparation of Polyurethane from 1,10-Dihydroxy-3-trifluoromethyl-3,4,4,5,5,6,6,7,7,8,8-undecafluorodecane and 3-Trifluoromethyl-3,4,4,5,5,6,6,7,7,8,8-undecafluorodecane-1,10-diisocyanate.

A mixture of 1,10-dihydroxy-3-trifluoromethyl-3,4,4,5,5,6,6,7,7,8,8-undecafluorodecane (448.7 mg, 0.9153 mmol) and 3-trifluoromethyl-3,4,4,5,5,6,6,7,7,8,8-undecafluorodecane-1,10-diisocyanate (403 mg, 0.9152 mmol) was heated to 30° C. to form a clear solution. Dibutyltin dilaurate in dichloromethane (5 ml of 0.086M solution in dichloromethane) was added and the mixture was allowed to react at ambient temperature for 16 hours and at 60° C. for 6 hours. The polymer, a clear, transparent, flexible elastomer, exhibited a glass transition at 13.80° C. The polymer was soluble in boiling THF and DMF.

EXAMPLE XIX

Preparation of Polyurethane from 1,12-Dihydroxy-3,5-bis(trifluoromethyl)-3,4,4,5,5,6,6,7,7,8,8,9,9,10,10-tetradecafluorododecane and 3-Trifluoromethyl-3,4,4,5,5,6,6,7,7,8,8-undecafluorodecane-1,10-diisocyanate.

A mixture of 1,12-dihydroxy-3,5-bis(trifluoromethyl)-3,4,4,5,6,6,7,7,8,8,9,9,10,10-tetradecafluorododecane (443.5 mg, 0.7512 mmol) and 3-trifluoromethyl-3,4,4,5,5,6,6,7,7,8,8-undecafluorodecane-1,10-diisocyanate (368.6 mg, 0.7519 mmol) was heated at 30° C. to form a homogeneous solution. Dibutyltin dilaurate (5 mL of 0.086M solution in dichloromethane) was added and the mixture was allowed to react at ambient temperature for 24 hours and at 60° C. for 6 hours. The polymer, a transparent elastomer exhibited a glass transition at 11.1° C.

EXAMPLE XX

Preparation of Polyurethane from 1,10-Dihydroxy-3,4,4,5,5,6,6,7,7,8,8-undecafluorodecane and 5-Isocyanato-1-(isocyanatomethyl)-1,3,3-trimethylcyclohexane.

A mixture of 1,10-dihydroxy-3,4,4,5,5,6,6,7,7,8,8-undecafluorodecane (1.00 g, 2.272 mmol) and 5-isocyanato-1-(isocyanatomethyl)-1,3,3-trimethylcyclohexane (516.1 mg, 98% pure, 2.275 mmol) was heated at 60° C. to form a clear solution. Dibutyltin dilaurate (5 mL of 0.086M solution in dichloromethane) was added and the mixture was heated at 60° C. for 24 hours. A clear, brittle plastic was obtained. The material exhibited a glass transition temperature of 56.12° C.

EXAMPLE XXI

Preparation of Polyurethane from 1,12-Dihydroxy-3,5-bis(trifluoromethyl)-3,4,4,5,6,6,7,7,8,8,9,9,10,10-tetradecafluorododecane and 5-Isocyanato-1-(isocyanatomethyl)-1,3,3-trimethylcyclohexane.

A mixture of 1,12-dihydroxy-3,5-bis(trifluoromethyl)-3,4,4,5,6,6,7,7,8,8,9,9,10,10-tetradecafluorododecane (1.00 g, 1.695 mmol) and 5-isocyanato-1-(isocyanatomethyl)-1,3,3-trimethylcyclohexane (385.7 mg, 1.700 mmol) was heated at 60° C. to form a clear solution. Dibutyltin dilaurate (10 mL of 0.086M solution in dichloromethane) was added and the mixture was allowed to react at 60° C. for 48 hours. A transparent, brittle plastic was obtained. The material exhibited a glass transition temperature of 40.35° C.

EXAMPLE XXII

Preparation of Polyurethane from 1,12-Dihydroxy-3,5-bis(trifluoromethyl)-3,4,4,5,6,6,7,7,8,8,9,9,10,10-tetradecafluorododecane and Methylenephenylene Diisocyanate.

A mixture of 1,12-dihydroxy-3,5-bis(trifluoromethyl)-3,4,4,5,6,6,7,7,8,8,9,9,10,10-tetradecafluorododecane (1.0 g, 1.695 mmol) and methylenephenylene diisocyanate (425 mg, 1.698 mmol) was reacted with bibutyltin dilaurate (3 mL of 0.086M solution in dichloromethane) at 75° C. for 32 hours. A yellow-colored, brittle plastic was obtained. The material exhibited a glass transition temperature of 72.5° C. and a melting point of 131° C. to 166° C.

While selected embodiments of our invention have been described in detail herein, it should, as previously indicated, be understood that the invention is not limited to those specific embodiments but is broad enough in concept to include modifications thereof within its scope, as taught herein and outlined by the language of the following claims. As an example, ethylene-inserted diiodide adducts in accordance with this invention having the formula I—CH$_2$CH$_2$—R—CH$_2$CH$_2$—I, in which R is a branched-chain perfluoroalkyl radical, can be prepared from an adduct of $\alpha,\omega$-diiodoperfluoroalkane having the formula I(CF$_2$)$_n$I, wherein n is a whole number of from 2 to 12, inclusive, and CF$_2$=CF(CF$_2$)$_n$F, wherein n is a whole number of from 1 to 10, inclusive.

. We claim:

1. A new composition of matter selected from the group consisting of I—$CH_2CH_2$—R—$CH_2CH_2$—I, which is an ethylene-inserted diiodide adduct of an α,ω-diiodoperfluoroalkane having the formula I($CF_2$)$_n$I, wherein n is a whole number of from 2 to 12, inclusive, and $CF_2$=$CF(CF_2)_n$F, wherein n is a whole number of from 1 to 10, inclusive, R being a branched-chain perfluoroalkyl radical; HO—$CH_2CH_2$—R—$CH_2CH_2$—OH; $H_2N$—$CH_2CH_2$—R—$CH_2CH_2$—$NH_2$; and OCN—$CH_2CH_2$—R—$CH_2CH_2$—NCO, wherein R, each instance, is the same as defined above.

2. As a new composition of matter in accordance with claim 1, an ethylene-inserted diiodide adduct having the formula I—$CH_2CH_2$—R—$CH_2CH_2$—I wherein the diiodide adduct is an adduct of 1,4-diiodoperfluorobutane and perfluoropropylene.

3. As a new composition of matter in accordance with claim 1, a diol having the formula HO—$CH_2CH_2$—R—$CH_2CH_2$—OH which is derived from an ethylene-inserted diiodide adduct having the formula I—$CH_2CH_2$—R—$CH_2CH_2$—I, wherein said diiodide adduct is an adduct of 1,4-diiodoperfluorobutane and perfluoropropylene.

4. As a new composition of matter in accordance with claim 1, a diamine having the formula $H_2N$—$CH_2CH_2$—R—$CH_2CH_2$—$NH_2$ which is derived from an ethylene-inserted diiodide adduct having the formula I—$CH_2CH_2$—R—$CH_2CH_2$—I, wherein said diiodide adduct is an adduct of 1,4-diiodoperfluorobutane and perfluoropropylene.

5. As a new composition of matter in accordance with claim 1, a diisocyanate having the formula OCN—$CH_2CH_2$—R—$CH_2CH_2$—NCO which is derived from $H_2N$—$CH_2CH_2$—R—$CH_2CH_2$—$NH_2$ which, in turn, is derived from an ethylene-inserted diiodide adduct having the formula I—$CH_2CH_2$—R—$CH_2CH_2$—I, wherein said diiodide adduct is an adduct of 1,4-diiodoperfluorobutane and perfluoropropylene.

* * * * *